US012569685B2

(12) United States Patent
Gunduz et al.

(10) Patent No.: US 12,569,685 B2
(45) Date of Patent: Mar. 10, 2026

(54) SIMULTANEOUS BILATERAL STIMULATION USING NEUROSTIMULATOR

(71) Applicant: University of Florida Research Foundation, Inc., Gainesville, FL (US)

(72) Inventors: Aysegul Gunduz, Gainesville, FL (US); Jackson N. Cagle, Gainesville, FL (US); Michael S. Okun, Gainesville, FL (US); Kelly D. Foote, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 608 days.

(21) Appl. No.: 17/920,102

(22) PCT Filed: Apr. 19, 2021

(86) PCT No.: PCT/US2021/027918
§ 371 (c)(1),
(2) Date: Oct. 20, 2022

(87) PCT Pub. No.: WO2021/216423
PCT Pub. Date: Oct. 28, 2021

(65) Prior Publication Data
US 2023/0166112 A1 Jun. 1, 2023

Related U.S. Application Data

(60) Provisional application No. 63/012,575, filed on Apr. 20, 2020.

(51) Int. Cl.
*A61N 1/36* (2006.01)

(52) U.S. Cl.
CPC .............................. *A61N 1/36171* (2013.01)

(58) Field of Classification Search
CPC . A61N 1/323; A61N 1/36171; A61N 1/36082
See application file for complete search history.

(56) References Cited

U.S. PATENT DOCUMENTS

| | | | |
|---|---|---|---|
| 9,511,223 B2 | 12/2016 | DeGiorgio et al. | |
| 2006/0149337 A1* | 7/2006 | John .................. | A61N 1/37235 |
| | | | 607/45 |

(Continued)

FOREIGN PATENT DOCUMENTS

| | | |
|---|---|---|
| WO | 2013152316 A1 | 4/2013 |
| WO | 2019244099 A2 | 12/2019 |

OTHER PUBLICATIONS

International Search Report for PCT/US21/27918 mailed Aug. 6, 2021.

(Continued)

*Primary Examiner* — George R Evanisko
(74) *Attorney, Agent, or Firm* — Thomas | Horstemeyer, LLP

(57) ABSTRACT

Various examples are provided for simultaneous bilateral brain stimulation. In one example, a method includes applying a first stimulation signal at a first frequency through a feature-side implanted neural stimulator (INS) on a first side of a brain, applying a second stimulation signal at a second frequency through a non-feature-side INS on a second side of the brain, and detecting a stimulation interference signal with the non-feature-side INS. The first stimulation signal can be a pulsed signal and the second simulation signal can be a continuous signal at a low stimulation voltage, and the stimulation interference signal at an interference frequency based upon the first and second frequencies. In another example, a neural stimulation system including a feature-side neural stimulator and a non-feature-side neural stimulator implanted on first and second sides of the brain and (Continued)

neural stimulation circuitry coupled to the neural stimulators.

20 Claims, 3 Drawing Sheets

(56) References Cited

U.S. PATENT DOCUMENTS

| | | |
|---|---|---|
| 2010/0114196 A1 | 5/2010 | Burnes et al. |
| 2019/0269916 A1 | 9/2019 | Senderowicz et al. |
| 2019/0388692 A1 | 12/2019 | Dinsmoor et al. |

OTHER PUBLICATIONS

Peng, et al., "Innovations in electrical stimulation harnessneural plasticity to restore motor function", Bioelectronics in Medicine, vol. 1, Issue: 4, p. 251-263, Date: Dec. 2018.

A.Y.J.M. Smeets, A.A. Duits, A.F.G. Leentjens, K. Schruers, V. van Kranen-Mastenbroek, V. Visser-Vandewalle, Y. Temel, L. Ackermans, Thalamic Deep Brain Stimulation for Refractory Tourette Syndrome: Clinical Evidence for Increasing Disbalance of Therapeutic Effects and Side Effects at Long-Term Follow-Up, Neuromodulation Technol. Neural Interface. (2017). doi:10.1111/ner.12556.

F.T. Sun, M.J. Morrell, Closed-loop Neurostimulation: The Clinical Experience, Neurotherapeutics. 11 (2014) 553-563. doi:10.1007/s13311-014-0280-3.

S. Little, A. Pogosyan, S. Neal, B. Zavala, L. Zrinzo, M. Hariz, T. Foltynie, P. Limousin, K. Ashkan, J. FitzGerald, A.L. Green, T.Z. Aziz, P. Brown, Adaptive deep brain stimulation in advanced Parkinson disease., Ann. Neurol. 74 (2013) 449-57. doi: 10.1002/ana.23951.

P. Afshar, A. Khambhati, S. Stanslaski, D. Carlson, R. Jensen, D. Linde, S. Dani, M. Lazarewicz, P. Cong, J. Giftakis, P. Stypulkowski, T. Denison, A translational platform for prototyping closed-loop neuromodulation systems., Front. Neural Circuits. 6 (2012) 117. doi:10.3389/fncir.2012.00117.

J.A. Herron, M.C. Thompson, T. Brown, H.J. Chizeck, J.G. Ojemann, A.L. Ko, Chronic electrocorticography for sensing movement intention and closed-loop deep brain stimulation with wearable sensors in an essential tremor patient, J. Neurosurg. 127 (2017) 580-587. doi:10.3171/2016.8.JNS16536.

E. Ryapolova-Webb, P. Afshar, S. Stanslaski, T. Denison, C. De Hemptinne, K. Bankiewicz, P.A. Starr, Chronic cortical and electromyographic recordings from a fully implantable device: Preclinical experience in a nonhuman primate, J. Neural Eng. 11 (2014) 016009. doi:10.1088/1741-2560/11/1/016009. (Abstract Only).

\* cited by examiner

Stimulation Detector "Stimulation Follower"

Adaptive Stimulation based on stimulation artifacts

160Hz Stimulation

Symptom Feature Detector "Stimulation Driver"

Adaptive Stimulation based on symptom features

170Hz Stimulation

Interference between Driver and Follower

Modulated frequency peak at 5Hz

SIMULTANEOUS BILATERAL STIMULATION USING NEUROSTIMULATOR

CROSS REFERENCE TO RELATED APPLICATIONS

This application is the 35 U.S.C. § 371 national stage application of PCT Application No. PCT/US2021/027918, filed Apr. 19, 2021, which claims priority to, and the benefit of, U.S. Provisional Application No. 63/012,575, filed Apr. 20, 2020, both of which are hereby incorporated by reference herein in their entireties.

STATEMENT REGARDING FEDERALLY SPONSORED RESEARCH OR DEVELOPMENT

This invention was made with Government support under grant nos. R01 NS096008 and NS095553 awarded by the National Institutes of Health. The government has certain rights in the invention.

BACKGROUND

Deep brain stimulation (DBS) is a promising neuromodulation treatment for patients with movement disorders suffering medical refractory symptoms. An implanted neural stimulator (INS) is surgically implanted in the patient to deliver continuous electrical current to suppress pathological activity in the deep brain structure thought to be responsible for the symptoms. However, the conventional DBS treatment also lead to more frequent battery replacement surgeries and numerous psychiatric side effects associate with continuous electrical stimulation, including visual disturbances, fatigue, and sleeping disorders.

SUMMARY

Aspects of the present disclosure are related to simultaneous bilateral brain stimulation. In one aspect, among others, a method for bilateral closed-loop stimulation comprises applying a first stimulation signal at a first frequency through a feature-side implanted neural stimulator (INS) on a first side of a brain, where the first stimulation signal is a pulsed signal; applying a second stimulation signal at a second frequency through a non-feature-side implanted neural stimulator (INS) on a second side of the brain, where the second simulation signal is a continuous signal at a low stimulation voltage ($V_L$); and detecting a stimulation interference signal with the non-feature-side INS, the stimulation interference signal at an interference frequency based upon the first and second frequencies. The method can comprise increasing the second stimulation signal to a therapeutic stimulation voltage ($V_H$) in response to detecting a therapeutic event based upon the stimulation interference signal.

In one or more aspects, the interference frequency can be about half of a difference between the first and second frequencies. The difference between the first and second frequencies can be about 10 Hz or less. The stimulation interference signal can be bandpass filtered. In various aspects, the first frequency can be greater than the second frequency. The second frequency can be a therapeutic stimulation frequency associated with the brain. The first frequency can be about 170 Hz, the second frequency can be about 160 Hz, and the interference frequency can be about 5 Hz. The first frequency can be less than the second frequency. In some aspects, the stimulation interference signal can be delayed by about one sampling period of the feature-side INS. The first stimulation signal can be applied over pulse intervals of about 1 second ON and about 3 seconds OFF.

In another aspect, a neural stimulation system comprises a feature-side neural stimulator implanted on a first side of the brain; a non-feature-side neural stimulator implanted on a second side of the brain; and neural stimulation circuitry coupled to the feature-side neural stimulator and non-feature-side neural stimulator. The neural stimulation circuitry can be configured to: apply a first stimulation signal at a first frequency to the first side of the brain through the feature-side neural stimulator, where the first stimulation signal is a pulsed signal; apply a second stimulation signal at a second frequency to the second side of the brain through the non-feature-side neural stimulator, where the second simulation signal is a continuous signal at a low stimulation voltage ($V_L$); and detect a stimulation interference signal via the non-feature-side neural stimulator, the stimulation interference signal at an interference frequency based upon the first and second frequencies. In some aspects, the first stimulation signal can be applied over pulse intervals with an OFF duration that is greater than an ON duration. The first stimulation signal can be applied over pulse intervals of about 1 second ON and about 3 seconds OFF.

In one or more aspects, the neural stimulation circuitry can be configured to increase the second stimulation signal to a therapeutic stimulation voltage ($V_H$) in response to detecting a therapeutic event based upon the stimulation interference signal. The stimulation interference signal can be bandpass filtered. The stimulation interference signal can be delayed by about one sampling period of the feature-side neural stimulator. A difference between the first and second frequencies can be about 20 Hz or less. In various aspects, the first frequency can be greater than the second frequency. The second frequency can be a therapeutic stimulation frequency associated with the brain.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1A:
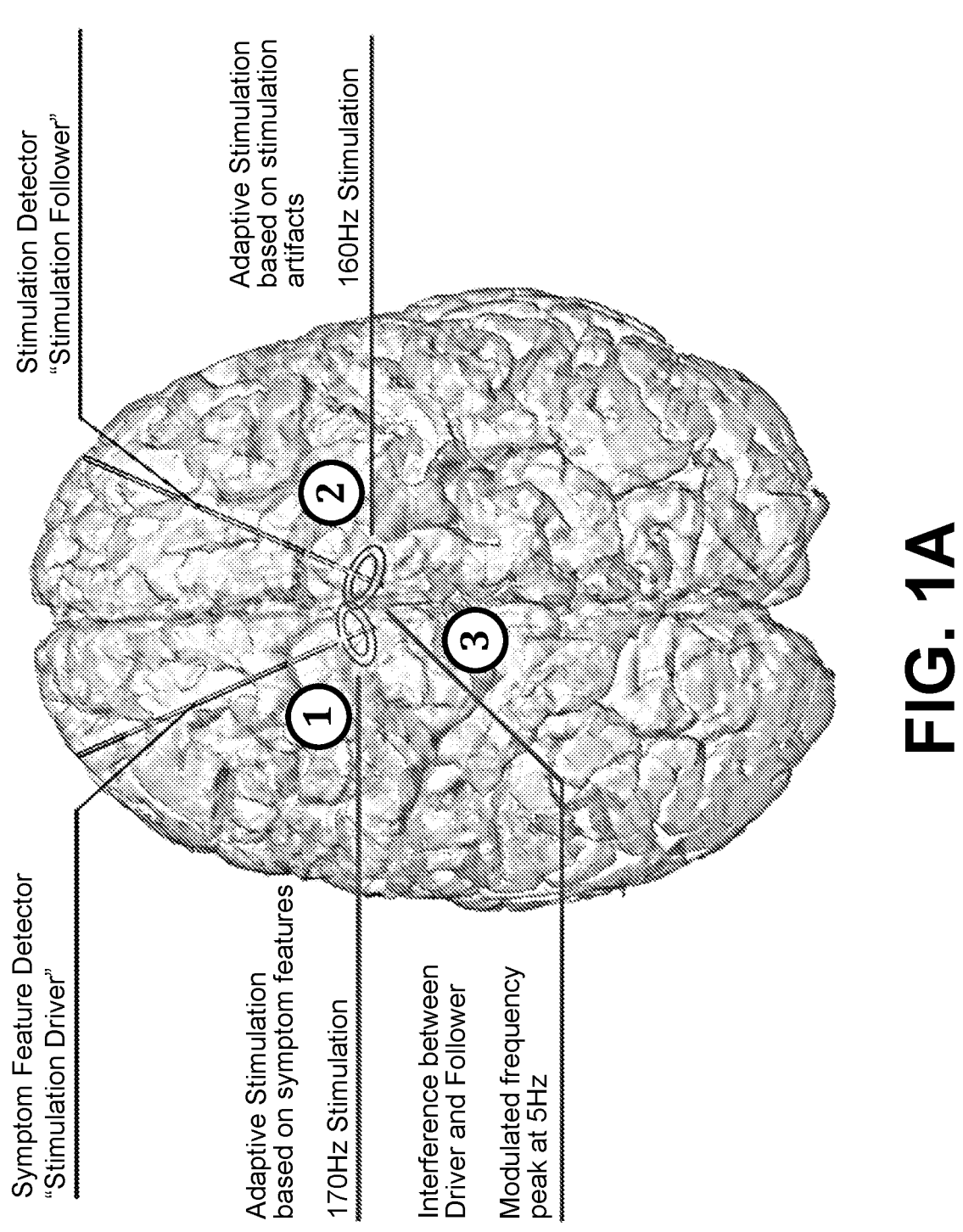
FIG. 1A illustrates an example of bilateral stimulation sensing in a patient with chronic deep brain stimulation (DBS) implants for a neurostimulator, in accordance with various embodiments of the present disclosure.

Disclosed herein are various examples related to simultaneous bilateral brain stimulation. Reference will now be made in detail to the description of the embodiments as illustrated in the drawings, wherein like reference numbers indicate like parts throughout the several views.

Due to the limitation of conventional deep brain stimulation (DBS) treatment, there is significant interest in developing improved DBS paradigms for treatment of movement disorders. Closed-loop DBS, or adaptive DBS therapy, is a technique that can deliver stimulation in response to physiological changes. Closed-loop DBS is thought to be a more effective and more efficient therapy than conventional DBS. Closed-loop DBS utilizes a computer-in-the-loop as a controller to determine when to deliver electrical stimulation based on the neural signal recording from the DBS leads. When the stimulation is not needed, the implanted neural stimulator (INS) can be set to a low stimulation voltage $(V_L)$. If the computer-in-the-loop detected a pathological signal from the brain, the INS can be set to a therapeutic stimulation voltage $(V_H)$. Such design significantly reduces the amount of electrical stimulation to the brain when no symptoms are present, therefore reducing the amount of side effects that the patients are suffering.

With DBS technologies and embedded systems, the closed-loop DBS can be achieved without the use of an external computer-in-the-loop. For example, Medtronic PC+S (Medtronic Neuromodulation, Minneapolis, MN) is an INS capable of both sensing neural signals and delivering electrical current based on the neural signals. The PC+S can provide an enabled chronic closed-loop DBS for improved treatment of various movement disorders. However, the Medtronic PC+S has limited channel configurations as it is only capable of connecting two 4-channel electrodes.

For studies that target bilateral brain regions while using other regions for closed-loop control, more than one PC+S can be used. For example, DBS therapy for Tourette Syndrome (TS) is known to be more beneficial to receive bilateral therapy than unilateral therapy, but deep electrodes are contaminated by the high stimulation power which requires the researchers to find closed-loop control feature from electrodes other than the stimulation sites. However, there is currently no communication protocol available between multiple PC+S devices to coordinate stimulation timing. This limitation prevents chronic bilateral closed-loop DBS with the current stimulation paradigm. Therefore, a new method is presented for delivering bilateral closed-loop DBS based on unilateral features using signal interference from electrical stimulations.

To perform bilateral closed-loop DBS, allow one device listening to the stimulation of the other device to follow the stimulation. Due to the narrow therapeutic stimulation frequency range for optimal treatment of a movement disorder patient, the stimulation frequency between two devices cannot differ too much, which will make the detection of stimulation difficult due to saturation of the sensing channel. For example, the difference can be about 20 Hz or less, about 15 Hz or less, or about 10 HZ or less. Larger frequency differences can also be used.

Signal interference is a condition that generates a low frequency envelope when two independent stimulation sources are delivering different frequencies of stimulation.

An oscillatory signal S can be described by its amplitude A and its frequency f, and the constructive and destructive interference of two signals $S_1$ and $S_2$ will result in a combined signal with interference described in the following equations:

$$S_1 = A_1\cos(2\pi f_1 t)$$
$$S_2 = A_2\cos(2\pi f_2 t)$$
$$SI = S_1 + S_2 = C\,\cos\left(2\pi\frac{(f_1+f_2)}{2}t\right)\cos\left(2\pi\frac{(f_1-f_2)}{2}t\right),$$

where the amplitude of the signal interference is proportion to the stimulation amplitude $A_1$ and $A_2$. The interference will generate oscillatory signals at shifted frequencies of $(f_1+f_2)/2$ and $(f_1-f_2)/2$, which are far enough from the actual stimulation frequencies $f_1$ and $f_2$ to prevent the therapeutic stimulation from saturating the bilateral DBS detection sensing channel. In practice, this difference of frequency should be far from the feature band of the sensing channel to avoid contamination of neural features as well.

To demonstrate the performance of the bilateral closed-loop DBS using signal interference as a detection method, a TS patient with chronic bilateral DBS implantation was selected for study. The patient was implanted with bilateral Medtronic PC+S. FIG. 1A illustrates the bilateral stimulation sensing in the TS patient with chronic DBS implants. Each PC+S was connected to a Medtronic RESUME II cortical strip over M1 and a Medtronic Model 3387 (Medtronic Neuromodulation, Minneapolis, MN) deep electrode in CM-Pf nuclei. During the post-operative monthly visit, the therapeutic stimulation parameters, including voltage (V) and pulse width (µs), for open-loop DBS were optimized by an experienced DBS programmer.

In the demonstration, the signal interference was implemented on the study participant whose therapeutic stimulation frequency was 160 Hz. The INS from the side with best performance in tic detection was coined the feature-side INS, also known as the "stimulation driver", and the other side was coined the non-feature-side INS, also known as the "stimulation follower". After identifying the feature-side INS, the therapeutic stimulation parameters for non-feature-side INS were programmed to have modified therapeutic-equivalent stimulation parameters. In this case, the stimulation frequency was modified to 170 Hz (providing a slight shift from the therapeutic frequency to maintain similar high-frequency therapeutic effect), and the stimulation voltage was modified to a voltage level that resulted in equivalent energy as the original therapeutic stimulation parameters.

As shown in FIG. 1A, the left thalamic electrode was chosen as the "stimulation driver" and right thalamic electrode was chosen as the "stimulation follower." Left thalamic electrode was chosen as the "stimulation driver" with 170 Hz stimulation and right thalamic electrode was chosen as the "stimulation follower" with 160 Hz stimulation. With the modified therapeutic-equivalent stimulation parameters, the signal interference will generate oscillatory signals at 5 Hz and 165 Hz. The 5 Hz interference generated by the interaction of two different stimulations can be used for sensing.

The performance of the bilateral DBS sensing was assessed by a 4-minute recording with the feature-side INS programmed to cycle the stimulation with pulse intervals of 1 second ON and 3 seconds OFF to mimic tic detections. Other pulse intervals (ON/OFF) may be used. The non-feature-side INS was programmed to sense the stimulation from the feature-side INS using a power channel with center frequency at 5.0 Hz and a 2.5 Hz bandwidth as the detector. The recordings from both INS were time-aligned using an external electromyogram (EMG) placed at the neck of the patient.

Figure 1B:
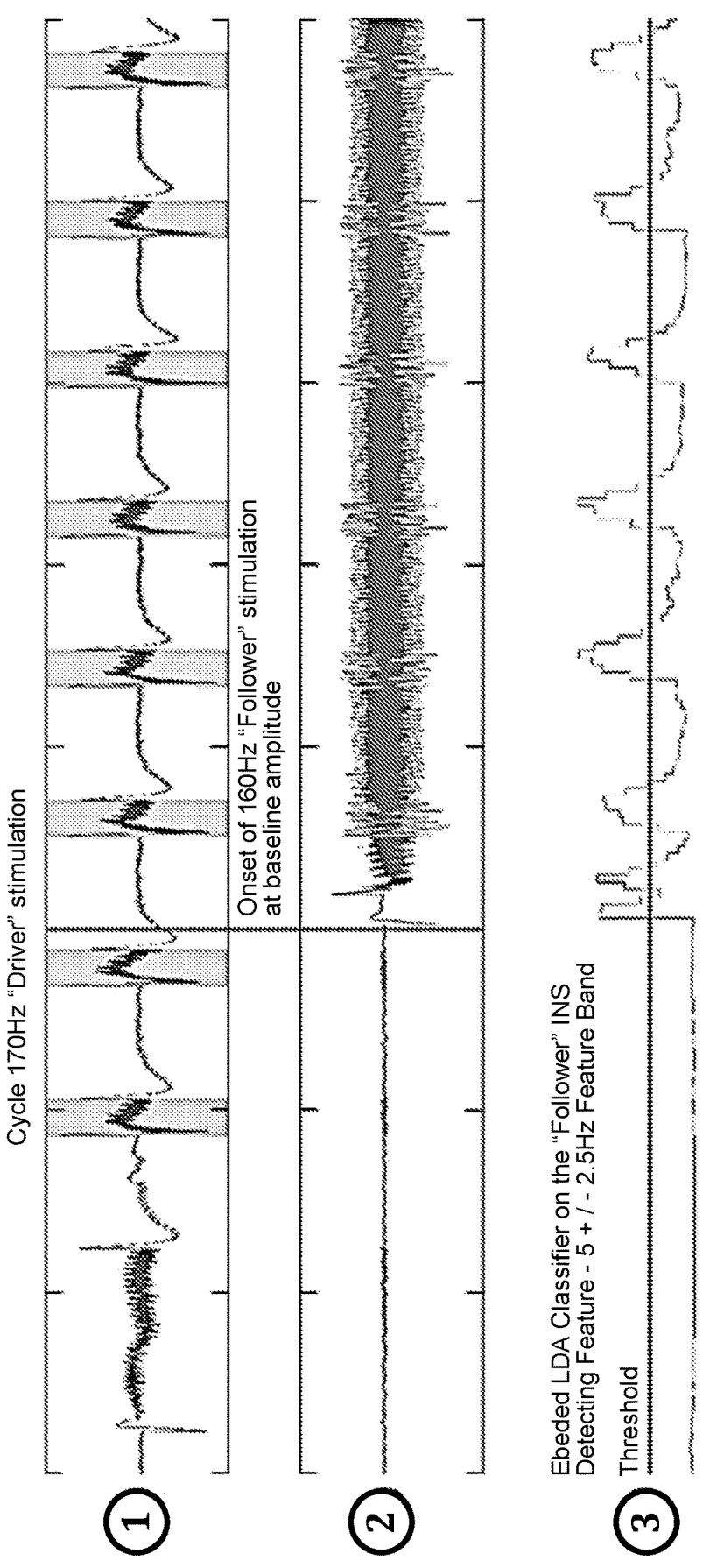
FIG. 1B illustrates an example of bilateral stimulation and sensing signals, in accordance with various embodiments of the present disclosure.

The stimulation is shown in FIG. 1B. The signal (1) for the left thalamic DBS, the feature-side DBS, was turned on with 170 Hz stimulation cycling first while right thalamic DBS was off. The signal (2) for the right thalamic DBS, the non-feature-side DBS, was turned on with 160 Hz stimulation a few cycles later. The interference signal (3) for the detector is activated on right thalamic DBS by sensing power at 5.0 Hz with the 2.5 Hz bandwidth. As shown in the first 15 seconds of FIG. 1B, the non-feature-side INS was not turned on (V=0V), therefore the interference signal was not generated. When the non-feature-side INS was turned on at 15 seconds with the low stimulation voltage, the detector could pick up the stimulation from feature-side INS consistently, except for the initial stimulation artifacts due to activation of stimulator.

Figure 2:
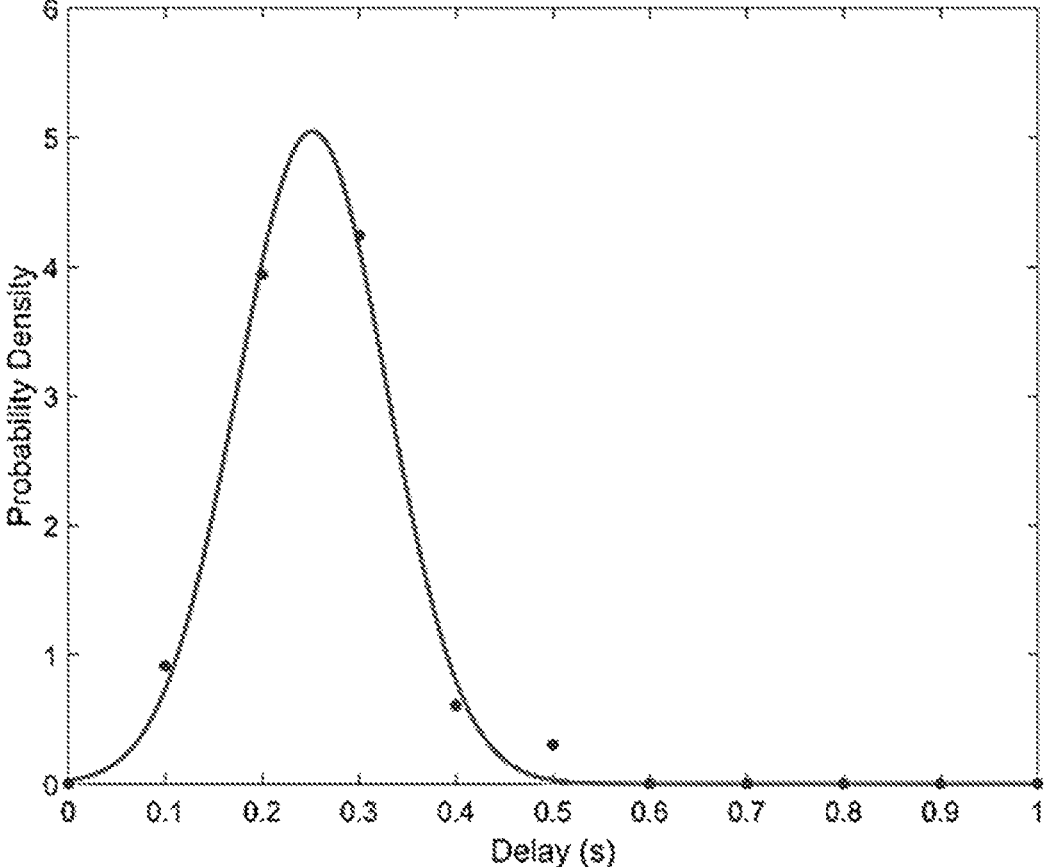
FIG. 2 illustrates an example of the sensing delay for the bilateral stimulation, in accordance with various embodiments of the present disclosure.

A 5 Hz interference could be identified from time channel recording and the 5.0 Hz power channel recording. The margin between stimulation on and off was over 300 units in the stimulation sensing power channel and could be easily distinguished by the on-board closed-loop detector on the Medtronic PC+S. The delay between stimulation onset and detection was computed across the 4 minutes recording, and a probability density function was created by fitting a gaussian curve to the estimated distribution function. The delay estimation is shown in FIG. 2, which illustrates the probability density function of the delay between non-feature-side INS detection and feature-side INS stimulation onset. A gaussian curve is fitted to the delay distribution, with mean of 0.257 seconds and standard deviation of 0.074 seconds. With the signal interference, feature-side INS stimulation can be detected from non-feature-side INS with a delay of 0.257±0.074 seconds. Given that the update rate of the sensing channel is 0.200 seconds, the actual delay is 1 sample point after stimulation onset from feature-side INS.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The term "substantially" is meant to permit deviations from the descriptive term that don't negatively impact the intended purpose. Descriptive terms are implicitly understood to be modified by the word substantially, even if the term is not explicitly modified by the word substantially.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A method for bilateral stimulation, comprising:
applying a first stimulation signal at a first frequency through a feature-side implanted neural stimulator (INS) on a first side of a brain, where the first stimulation signal is a pulsed signal comprising pulse intervals, each pulse interval having a defined ON period comprising a signal at the first frequency and a defined OFF period;
applying a second stimulation signal at a second frequency through a non-feature-side implanted neural stimulator (INS) on a second side of the brain, where the second stimulation signal is a continuous signal at a low stimulation voltage ($V_L$) at the second frequency; and
detecting a stimulation interference signal with the non-feature-side INS, the stimulation interference signal at an interference frequency based upon the first and second frequencies.

2. The method of claim 1, comprising
detecting a therapeutic event based upon the stimulation interference signal; and
increasing the second stimulation signal to a therapeutic stimulation voltage ($V_H$) in response to detecting the therapeutic event.

3. The method of claim 1, wherein the interference frequency is about half of a difference between the first and second frequencies.

4. The method of claim 3, wherein the difference between the first and second frequencies is about 10 Hz or less.

5. The method of claim 3, comprising bandpass filtering the stimulation interference signal.

6. The method of claim 1, wherein the first frequency is greater than the second frequency.

7. The method of claim 6, wherein the second frequency is a therapeutic stimulation frequency.

8. The method of claim 7, wherein the first frequency is about 170 Hz, the second frequency is about 160 Hz, and the interference frequency is about 5 Hz.

9. The method of claim 1, wherein the first frequency is less than the second frequency.

10. The method of claim 1, wherein the stimulation interference signal is delayed by about one sampling period of the feature-side INS.

11. The method of claim 1, wherein the defined ON period is about 1 second and the defined OFF period is about 3 seconds.

12. A neural stimulation system, comprising:
a feature-side neural stimulator configured to be implanted on a first side of a brain;
a non-feature-side neural stimulator configured to be implanted on a second side of the brain; and
neural stimulation circuitry coupled to the feature-side neural stimulator and non-feature-side neural stimulator, the neural stimulation circuitry configured to:
apply a first stimulation signal at a first frequency to the first side of the brain through the feature-side neural stimulator, where the first stimulation signal is a pulsed signal comprising pulse intervals, each pulse interval having a defined ON period comprising a signal at the first frequency and a defined OFF period;

apply a second stimulation signal at a second frequency to the second side of the brain through the non-feature-side neural stimulator, where the second stimulation signal is a continuous signal at a low stimulation voltage ($V_L$) at the second frequency; and detect a stimulation interference signal via the non-feature-side neural stimulator, the stimulation interference signal at an interference frequency based upon the first and second frequencies.

13. The neural stimulation system of claim 12, wherein the neural stimulation circuitry is configured to;

detect a therapeutic event based upon the stimulation interference signal; and increase the second stimulation signal to a therapeutic stimulation voltage ($V_H$) in response to detecting the therapeutic event.

14. The neural stimulation system of claim 13, comprising bandpass filtering the stimulation interference signal.

15. The neural stimulation system of claim 13, wherein the stimulation interference signal is delayed by about one sampling period of the feature-side neural stimulator.

16. The neural stimulation system of claim 12, wherein the first frequency is greater than the second frequency.

17. The neural stimulation system of claim 16, wherein the second frequency is a therapeutic stimulation frequency.

18. The neural stimulation system of claim 16, wherein a difference between the first and second frequencies is about 20 Hz or less.

19. The neural stimulation system of claim 18, wherein the defined ON period is about 1 second and the defined OFF period is about 3 seconds.

20. The neural stimulation system of claim 12, wherein the defined OFF period is greater than the defined ON period.

* * * * *